United States Patent [19]

Pfiffner et al.

[11] Patent Number: 5,606,095
[45] Date of Patent: Feb. 25, 1997

[54] 2-AMINOOXYMETHYLENEPHENYLACETIC ACID DERIVATIVES

[75] Inventors: Albert Pfiffner, Bülach, Switzerland; Stephan Trah, Freiburg, Germany; Hugo Ziegler, Witterswil, Switzerland

[73] Assignee: Ciba-Geigy Corporation, Tarrytown, N.Y.

[21] Appl. No.: 462,259

[22] Filed: Jun. 5, 1995

Related U.S. Application Data

[62] Division of Ser. No. 156,555, Nov. 23, 1993, abandoned.

[30] Foreign Application Priority Data

Dec. 1, 1992 [CH] Switzerland ............... 3683/92

[51] Int. Cl.$^6$ .................................................. C07C 229/00
[52] U.S. Cl. ............................................. 560/42; 562/451
[58] Field of Search ............................... 560/42; 562/451

[56] References Cited

U.S. PATENT DOCUMENTS

| | | | |
|---|---|---|---|
| 3,758,546 | 9/1973 | Kastreimer et al. | 260/471 R |
| 4,207,341 | 6/1980 | Hübner et al. | 424/319 |
| 5,055,471 | 10/1991 | de Fraine et al. | 514/255 |
| 5,157,144 | 10/1992 | Anthony et al. | 560/35 |
| 5,194,662 | 3/1993 | Brand et al. | 560/35 |
| 5,238,956 | 8/1993 | Clough et al. | 514/506 |

FOREIGN PATENT DOCUMENTS

| | | |
|---|---|---|
| 0460575 | 12/1991 | European Pat. Off. |
| 0463488 | 1/1992 | European Pat. Off. |
| 1276046 | 8/1968 | Germany. |
| 0403791 | 6/1966 | Switzerland. |
| WO9218487 | 10/1992 | WIPO. |
| WO9218494 | 10/1992 | WIPO. |

OTHER PUBLICATIONS

Houben Weyl "Methoden der organ Chemie" vol. x/1, pp. 1189–1192 (1976).
J. Chem. Soc. pp. 229–238 (1960).
March, Advanced Organic Chemistry, p. 320, 1977.

*Primary Examiner*—Gary Geist
*Assistant Examiner*—Barbara S. Frazier
*Attorney, Agent, or Firm*—Edward McC. Roberts

[57] ABSTRACT

2-Aminooxymethylenephenylacetic acid ester derivatives of the formula

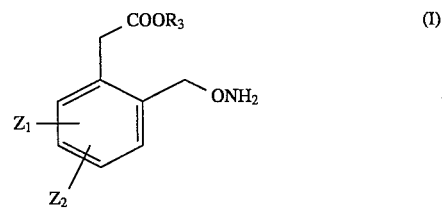

wherein $Z_1$ and $Z_2$ are hydrogen, halogen, hydroxy, $C_1$–$C_4$alkyl, $C_1$–$C_4$alkoxy, $C_1$–$C_4$haloalkyl, $C_1$–$C_4$haloalkoxy, $C_1$–$C_4$alkylcarbonyl, phenoxy, nitro or cyano, or $Z_1$ and $Z_2$, together with the linking phenyl radical, are naphthalene or hydrogenated naphthalene, and $R_3$ is hydrogen or $C_1$–$C_{12}$alkyl. The compounds of this invention may be used as the free base or as a protic acid salt and are important intermediates for the manufacture of microbicides for plant protection.

3 Claims, No Drawings

2-AMINOOXYMETHYLENEPHENYLACETIC ACID DERIVATIVES

This is a division of Ser. No. 08/156,555, filed Nov. 23, 1993 now abandoned.

The present invention relates to a 2-aminooxymethylenephenylacetic acid ester derivative of formula I

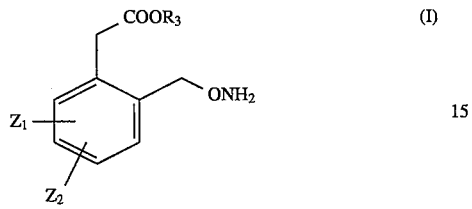

as free base and as salt with protic acids, to the preparation of this compound and to the use thereof for synthesising microbicides of formula VI useful in plant protection.

In the above formula $Z_1$ and $Z_2$ are hydrogen, halogen, hydroxy, $C_1$–$C_4$alkyl, $C_1$–$C_4$alkoxy, $C_1$–$C_4$haloalkyl, $C_1$–$C_4$haloalkoxy, $C_1$–$C_4$alkylcarbonyl, $C_1$–$C_4$alkoxycarbonyl, phenoxy, nitro, cyano, $Z_1$ and $Z_2$, together with the linking phenyl radical, are naphthalene or hydrogenated naphthalene, and $R_3$ is hydrogen or $C_1$–$C_{12}$alkyl.

Suitable salts are those with acids HY, where Y is the acid anion, typically hydrochloric acid, hydrobromic acid, hydriodic acid, perchloric acid, unsubstituted or substituted benzenesulfonic acid, methanesulfonic acid, trifluoromethanesulfonic acid, tetrafluoroboric acid, hexafluorophosphoric acid, phosphoric acid, sulfuric acid, sulfurous acid, carboxylic acids in general (e.g. formic acid, acetic acid, trifluoroacetic acid etc.). Mineral acids are preferred, in particular hydrochloric acid and sulfuric acid.

The inventive process consists in step A of the reaction of a substituted o-tolylacetate II with a benzoyl hydroxylamine III to give benzoylated 2-aminooxymethylenephenylacetates IV and, in step B, of the acid saponification (=hydrolysis) to give the final product I in accordance with Scheme 1

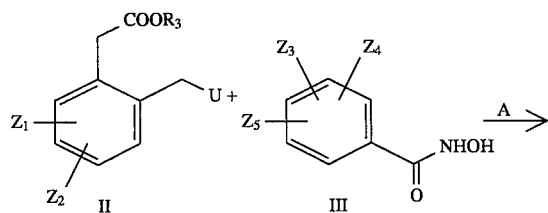

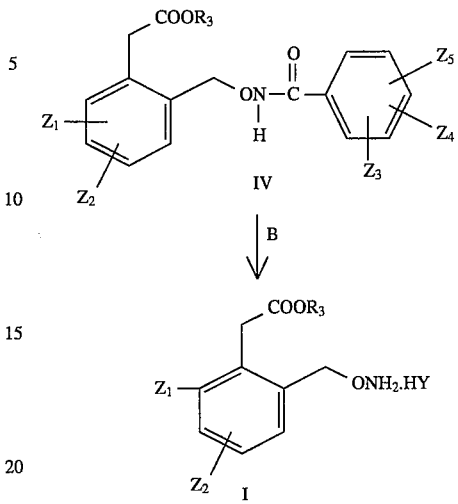

In the above formulae, U is a nucleofugic leaving group, $R_3$, $Z_1$ and $Z_2$ are as defined above, $Z_3$, $Z_4$ and $Z_5$ are identical or different and are hydrogen, unbranched or branched $C_1$–$C_6$alkyl, halogen, hydroxy, unbranched or branched $C_1$–$C_6$alkoxy, nitro, cyano, $N(R_5)_2$, $SO_2NH_2$, unsubstituted or substituted phenoxy, $CF_3$, mercapto, and both substituents $R_5$ are identical or different and are hydrogen and/or unbranched or branched $C_1$–$C_6$alkyl, and wherein also $Z_3$ and $Z_4$ in vicinal position together form a methylenedioxy bridge or, together with the linking phenyl ring can form a naphthyl ring.

Preferred substituents $Z_3$, $Z_4$ and $Z_5$ are hydrogen, methyl and halogen, most preferably hydrogen. $R_3$ is preferably hydrogen or $C_1$–$C_4$alkyl, most preferably methyl.

A nucleofugic leaving group U is suitably a halide, typically a chloride, bromide or iodide, also a benzenesulfonate, toluenesulfonate, methanesulfonate, triflate or acetate. A bromide is especially preferred.

In both partial steps A and B it is expedient to use a diluent and to carry out the reaction in the temperature range from 0° C. to the boiling point of the reaction mixture.

In partial step A it is useful to add an inorganic or an organic base or a mixture of bases, whereas the hydrolysis in partial step B is carried out under acidic conditions.

The novel process of this invention is distinguished in both partial steps A and B by easy accessibility of the reactants, a smooth preparative reaction and surprisingly high yields, even in those cases in which the starting material of formula II is used as impure crude product. The process thus constitutes a very substantial contribution to the simplified synthesis of the microbicidal 2-phenylacrylates, 2-phenylalkoxyacrylates and phenylmethoxyiminoacetates disclosed, inter alia, in WO 90/07493, EP-A-370 629, EP-A-414 153, EP-A-426 460, EP-A-460 575, EP-A-463 488, EP-A-472 300, WO 92/18494, WO 92/18487.

The compounds of formula I so obtained can be reacted, whether as bases or as salts, with aldehydes or ketones to corresponding aldimino or ketimino derivatives of formula V, from which the microbicides described in the literature references cited above are obtained in conventional manner by further reaction in the acetate side-chain (reaction sequences C and D):

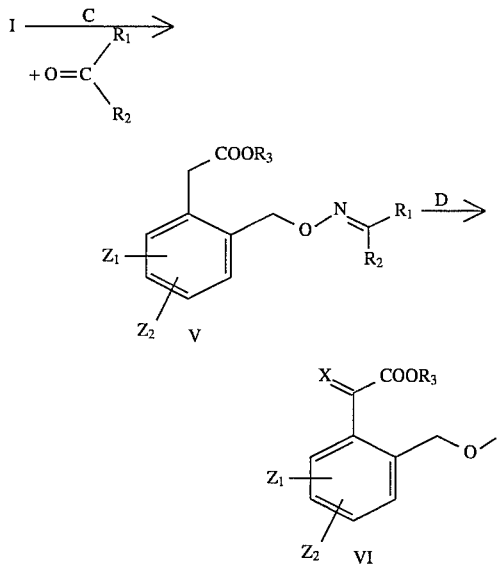

In the last formula VI, X is CHO($C_1$–$C_4$alkyl), NO($C_1$–$C_4$alkyl), or unsubstituted $CH_2$ or $CH_2$ which is substituted in another manner, $R_1$ and $R_2$ may be identical or different and are hydrogen, cyano, unbranched or branched $C_1$–$C_{10}$alkyl, $C_1$–$C_4$haloalkyl, $C_3$–$C_6$cycloalkyl, $C_3$–$C_6$halocycloalkyl, $C_3$–$C_6$cycloalkyl-$C_1$–$C_4$alkyl, $C_1$–$C_4$alkoxy-$C_1$–$C_4$alkyl, $C_1$–$C_4$alkylthio-$C_1$–$C_4$alkyl, $C_2$–$C_6$alkenyl, $C_2$–$C_5$haloalkenyl, $C_3$–$C_6$cycloalkenyl, $C_3$–$C_6$halocycloalkenyl, $C_2$–$C_6$alkynyl, $C_1$–$C_6$alkoxy, $C_1$–$C_6$haloalkoxy, $C_1$–$C_4$alkylthio, benzylthio, $C_1$–$C_4$alkylcarbonyl, unsubstituted or substituted phenylcarbonyl, unsubstituted or substituted benzylcarbonyl, $C_1$–$C_4$alkoxycarbonyl, unsubstituted or substituted phenoxycarbonyl, unsubstituted or substituted benzyloxycarbonyl, unsubstituted or substituted aryl, unsubstituted or substituted aryloxy, unsubstituted or substituted arylthio, unsubstituted or substituted aryl-$C_1$–$C_4$alkyl, unsubstituted or substituted aryl-$C_1$–$C_4$alkenyl, unsubstituted or substituted aryloxy-$C_1$–$C_4$alkyl, unsubstituted or substituted arylthio-$C_1$–$C_4$alkyl, unsubstituted or substituted heteroaryl, unsubstituted or substituted heteroaryloxy, unsubstituted or substituted heteroarylthio, unsubstituted or substituted heteroaryl-$C_1$–$C_4$alkyl, unsubstituted or substituted heteroaryl-$C_2$–$C_4$alkenyl, unsubstituted or substituted heteroaryloxy-$C_1$–$C_4$alkyl, unsubstituted or substituted heterocyclyl, unsubstituted or substituted heterocyclyloxy, unsubstituted or substituted heterocyclylalkyl, N($R_4$)$_2$, and the meanings of $R_4$ are identical or different and are H, $C_1$–$C_4$alkyl, unsubstituted or substituted phenyl, or both substituents $R_4$, together with the linking nitrogen atom, form a 5- to 7-membered unsubstituted or substituted ring that may contain hetero atoms; or $R_1$ and $R_2$ are —CON($R_4$)$_2$, nitro, halogen, —S(O)$_n$$R_4$, wherein n is 0, 1 or 2, or is (CH$_2$)$_m$PO(O$R_4$)$_2$, wherein m is 0 or 1, or $R_1$ and $R_2$ together form a carbocyclic or heterocyclic ring that may be unsubstituted or substituted, and $R_3$, $Z_1$ and $Z_2$ are as defined for formula I.

The invention also relates to the preparation of compounds of formula VI in accordance with reaction schemes A, B, C and D via the intermediates of formulae IV, I and V.

Accordingly, the invention further relates to a process for the preparation of the above defined compounds of formula VI, which comprises A) reacting a substituted o-tolylacetate of formula II

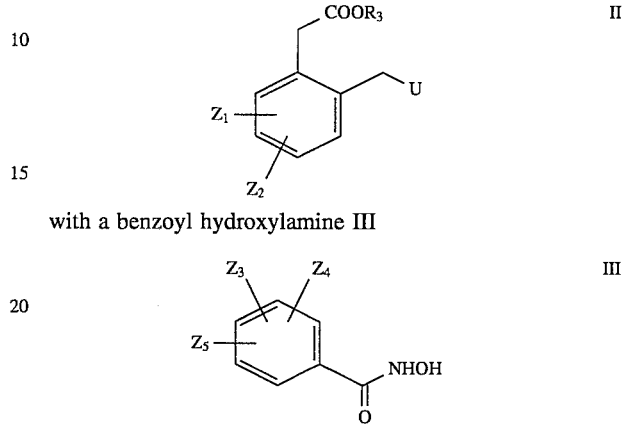

with a benzoyl hydroxylamine III

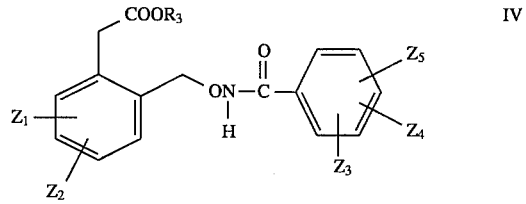

B) subjecting the benzoylated 2-aminooxymethylenephenylacetate so obtained of formula IV

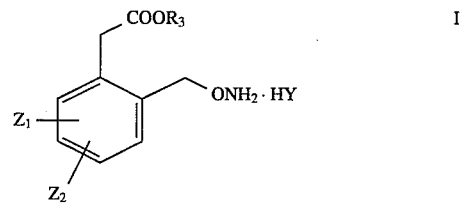

to acid saponification with an acid HY,

C) reacting the 2-aminooxymethylenephenylacetate of formula I

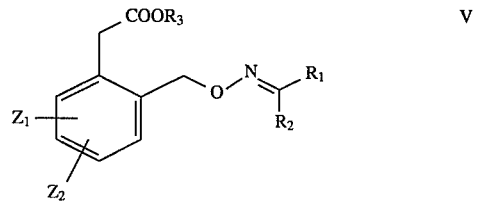

with a ketone $R_1$—CO—$R_2$, and

D) converting the acetate side-chain of the resultant intermediate V

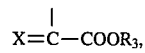

into the side-chain $$X=\overset{|}{C}-COOR_3,$$

wherein X is optionally $C_1$–$C_4$alkyl-O—CH or $C_1$–$C_4$alkyl-O—N, and $Z_1$ to $Z_5$ and $R_1$ to $R_3$ as well as U are as defined in connection with formulae I to V above, and Y is an acid anion.

The following complicated reaction schemes, which result in high losses in yield (incomplete reaction; side-reactions), have been proposed in the prior art literature for the synthesis of the compounds of formula VI.

Scheme II

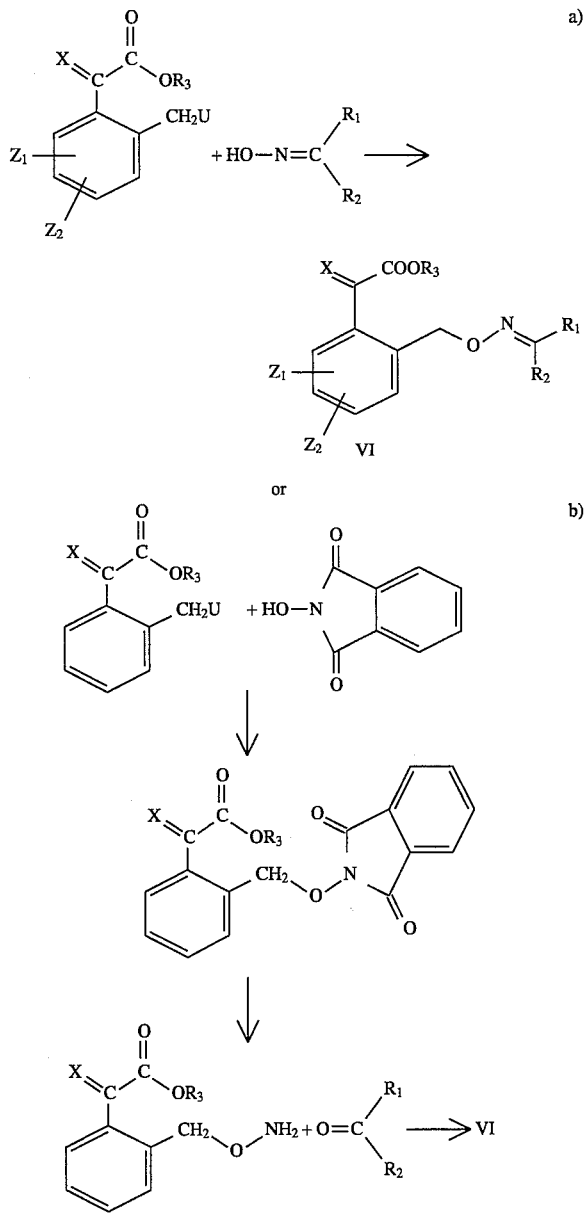

In contradistinction thereto, the process of this invention constitutes a substantial enrichment of the art.

Preparative Examples and explanations are provided hereinafter in connection with steps A, B, C and D.

Reaction sequence A:

The compounds of the general formula II and III, wherein $Z_1$ to $Z_5$, $R_3$ and U are as defined above, are conveniently reacted in the presence of a base. A suitable inorganic or organic base is typically an alkali metal or alkaline earth metal compound such as a hydroxide, oxide or carbonate of lithium, sodium, potassium, magnesium, calcium, strontium and barium or also hydrides such as sodium hydride, and also oxides such as ZnO, $Al_2O_3$, $Ag_2O$ and the like. Suitable organic bases typically include $NH_3$, alkylamine, dialkylamine, piperidine, quinoline, tertiary amines such as triethylamine, triethylenediamine, pyridine, 4-dimethylaminopyridine, also alcoholates such as $NaOCH_3$, NaOEt, potassium tert-butylate and the like.

Although it is not mandatory, solvents or diluents can be used with advantage for the reaction. Illustrative examples of suitable solvents and diluents are: halogenated hydrocarbons, preferably chlorinated hydrocarbons such as tetrachloroethylene, tetrachloroethane, dichloropropane, dichloromethane, dichlorobutane, chloroform, carbon tetrachloride, trichloroethane, trichloroethylene, pentachloroethane, 1,2-dichloroethane, 1,1-dichloroethane, 1,2-cis-dichloroethylene, chlorobenzene, fluorobenzene, bromobenzene, dichlorobenzene, dibromobenzene, chlorotoluene, trichlorotoluene; ethers such as ethyl propyl ether, methyl tert-butyl ether, n-butyl ethyl ether, di-n-butyl ether, diisobutyl ether, diisoamyl ether, diisopropyl ether, anisole, cyclohexyl methyl ether, diethyl ether, ethylene glycol dimethyl ether, tetrahydrofuran, dioxane, thioanisole, dichlorodiethyl ether, nitrated hydrocarbons such as nitromethane, nitroethane, nitrobenzene, chloronitrobenzene, o-nitrotoluene; nitriles such as acetonitrile, butyronitrile, isobutyronitrile, benzonitrile, m-chlorobenzonitrile; aliphatic, aromatic or cycloaliphatic hydrocarbons such as heptane, hexane, octan, nonane, cymene, petroleum fractions having a boiling range from 70° C. to 190° C., benzene, toluene, cyclohexane, methyl cyclohexane, decaline, petroleum ether, ligroin, trimethylpentanes such as 2,3,3-trimethylpentane; esters such as ethyl acetate, isobutyl acetate; amides, e.g. formamide, N-methylformamide, N-methylpyrrolidone, dimethyl formamide; ketones such as acetone, methyl ethyl ketone; dimethyl sulfoxide. Mixtures of the cited solvents and diluents may also suitably be used.

The reaction temperatures are preferably in the range from 0° C. to the boiling temperature of the diluent.

Especially preferred bases in reaction step A are alkali metal carbonates, most preferably sodium carbonate or potassium carbonate, and a preferred diluent is acetonitrile, especially in the temperature range from 60° C. to 65° C.

The isolation of the compound of formula IV can be effected by methods which are known per se, conveniently by removing the diluent by evaporation and taking up the residue in ethyl acetate and then washing the organic extract with aqueous potassium carbonate solution. After drying over a drying agent such as sodium sulfate, the organic phase is concentrated by evaporation. The resultant hydroxamate of formula IV—and this is an important advantage of the inventive process—can be used further direct without additional purification.

The starting materials of formulae II and III are either known or can be prepared by known methods (q.v. inter alia Org. Synth. Coll. Vol. II, 67 and J. Am. Chem. Soc. 31, 3759 (1966)).

Reaction sequence B:

The crude product of formula IV obtained in sequence A, wherein $Z_1$–$Z_5$ and $R_3$ are as defined above, is saponified to the compound of the general formula I, wherein $Z_1$, $Z_2$, $R_3$ and Y have the given meanings, in a diluent that is preferably an alcohol of formula $R_3$—OH to which a further solvent as indicated in A) may be added, in the presence of an acid of formula HY, wherein Y is the anion of the acid, at a reaction temperature in the range from 0° C. to the boiling point of the diluent, preferably from 20° C. to the reflux temperature of the diluent.

Suitable acids HY are conveniently hydrohalic acids (hydrochloric, hydrobromic or hydriodic acid), sulfonic acids (unsubstituted or substituted benzenesulfonic acid, methanesulfonic acid, trifluoromethanesulfonic acid), carboxylic acids, (formic acid, acetic acid, trifluoroacetic add), perchloric acid, tetrafluoroboric acid, phosphoric acid, hexafluorophosphoric acid, sulfuric acid or sulfurous acid. This recitation implies no limitation with respect to the use of other possible acids.

Reaction sequence C:

The salt of formula I obtained in sequence B can be reacted with a ketone of formula VII $$\begin{array}{c} R_1 \\ \phantom{R}\rangle{=}O \\ R_2 \end{array} \qquad VII$$

wherein $R_1$ and $R_2$ are as previously defined, in an inert diluent such as an ether (e.g. tetrahydrofuran or dioxane or dimethoxy ether), an ester (e.g. ethyl acetate), a halogenated hydrocarbon (e.g. 1,2-dichloroethane or chloroform or methylene chloride), an amide (e.g. dimethylformamide or N-methylpyrrolidone), an aromatic compound (e.g. benzene or toluene), acetonitrile, dimethyl sulfoxide, and in the presence of a base as defined in sequence A. It is preferred to carry out the reaction in pyridine that simultaneously acts as diluent and base. The reaction takes place in the temperature range from 0° C. to the temperature of the diluent or the base. The preferred temperature range is from 50° C. to the reflux temperature of the diluent. If the reaction is carded out in pyridine, the temperature range from 80° C. to 116° C. is especially preferred.

The products of the general formula V can be isolated and purified by known methods by distilling off the diluent and taking up the residue in water. After acidification and extraction, the resultant crude product can be purified by known methods, typically by distillation or chromatography. The product can be obtained as a mixture of isomers (E/Z).

Reaction sequence D:

a) The acetate side-chain of the intermediate of formula V obtained in sequence C can be convened by customary methods into a hydroxyacrylate side-chain. The process comprises treating the intermediate of formula V with methyl formate in the presence of a strong base such as sodium alcoholate (preferably sodium methylate) or NaH, NaNH$_2$, potassium tert-butylate etc. Particularly suitable solvents are polar types such as dimethyl formamide, ethers (tetrahydrofuran, dioxane etc), alcohols such as tert-butanol or methanol, and ketones such as tert-butyl methyl ketone. The reaction temperature is in the range from −10° C. to +60° C., preferably from 0° C. to 40° C.

The subsequent alkylation to the alkoxyacrylate side-chain can conveniently be effected with alkyl iodide or diazomethane. The methoxyacrylate is obtained by suitably using dimethyl sulfate in basic medium with an alkyl cyanide as solvent, preferably acetonitrile. The reaction temperature is in the range from 0° C. to +70° C.

b) The acetate side-chain of the intermediate of formula V obtained in sequence C can be converted with nitrite in basic medium into the hydroxyiminoglyoxylate side-chain, which can be alkylated in the same manner as described in a). Alkyl nitrites such as ethyl nitrite, tert-butyl nitrite, isopentyl nitrite etc., in the presence of a base such as NaOH, KOH, NaH, alkali metal alcoholate (e.g. potassium tert-butylate or NaOCH$_3$), are suitably used to introduce the hydroxyimino group. The reaction temperature is in the range from −10° C. to +60° C., preferably from 0° C. to 40° C. Inert polar solvents can be used, typically ethers, alcohols and ketones, preferably those types referred to in a).

PREPARATIVE EXAMPLES

Example 1

(Reaction sequence A)

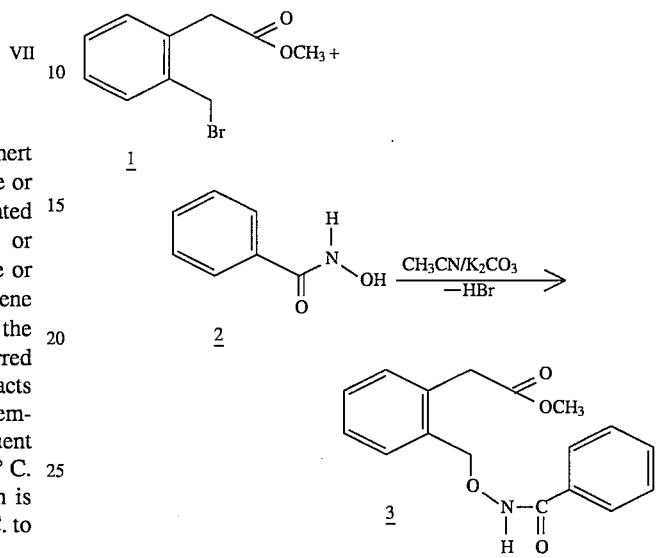

A mixture of 102 g (0.74 mol) of benzohydroxamic acid 2, 111 g (0.80 mol) of pulverised potassium carbonate and 1400 ml of acetonitrile is heated to 60° C. After 0.5 h, 162 g of methyl o-bromomethylphenylacetate 1, which is obtained as 68% crude product from the bromination of methyl o-tolylacetate with N-bromosuccinimide, dissolved in 100 ml of acetonitrile, is added dropwise over 0.5 h at 60° C.–65° C. and the reaction mixture is stirred for 5.5 h at this temperature.

For working up, the reaction mixture is cooled to 25° C., filtered through Hyflo Super Cel and concentrated by evaporation under a water jet vacuum. The residual oil is taken up in 1000 ml of ethyl acetate. After washing with 500 ml of a 6% solution of potassium carbonate, the phases are separated and the aqueous phase is extracted once with 300 ml of ethyl acetate. The combined organic phases are washed once with 200 ml of water, dried over sodium sulfate, filtered and evaporated to dryness, giving 182 g of the benzohydroxamate 3 in the form of an orange oil. No further purification of the product is effected.

Example 2

(Reaction sequence B)

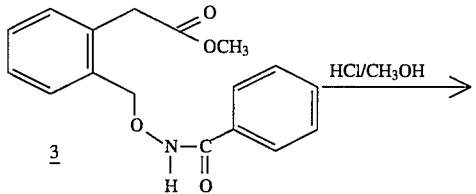

9
-continued

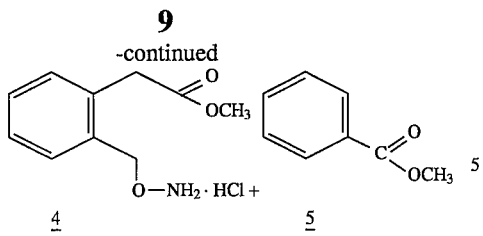

10
-continued

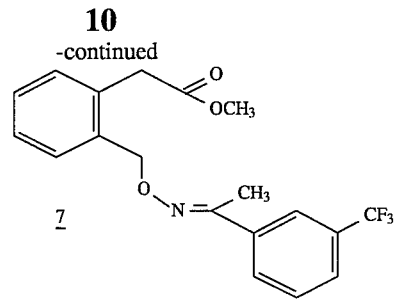

A solution of 182 g of the impure benzohydroxamate 3 obtained in Example 1 and 900 ml of 8% hydrochloric acid in methanol is heated to 60° C. After 1 hour, excess methanol is stripped off and the residue consisting of the amine hydrochloride 4 and methyl benzoate 5 is stirred with 500 ml of diethyl ether for 0.5 h at 35° C. The tacky precipitate of the amine hydrochloride 4 is cooled to 20° C., separated from the ether solution and digested with 500 ml of tetrahydrofuran at 40°–50° C. The batch is then cooled and filtered, giving 65.5 g (=62% of theory, starting from the bromide 1) of a fine, pale greenish crystal powder with a melting point of 157°–158° C. (dec.).

The reaction sequences A and B are distinguished by the feature that readily accessible and cheap starting materials and auxiliaries are used. One material advantage over the prior art methods of synthesising the compounds of formula VI is the possibility of using the unpurified crude product obtained from the bromination of methyl o-tolylacetate with N-bromosuccinimide (NBS) and still obtaining 4 in high yield (c .60–70%) via both sequences A and B.

The second material advantage over known prior art processes for the preparation of the compound of formula VI resides in having available in 4 a compound that makes it possible to obtain compounds of formula VI in reasonable yield even using those ketones

with which a reaction as oxime in accordance with scheme II a) is not possible at all or is carried out only in unsatisfactory yield.

Example 3

(Reaction sequence C)

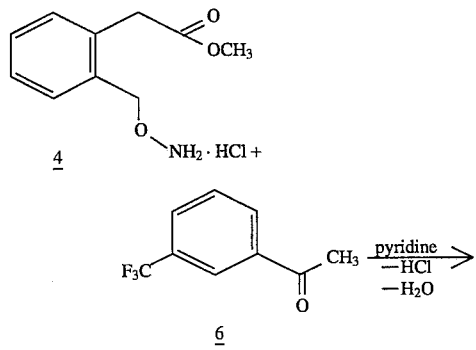

To a solution of 53.1 g (0.282 mol) of 3-trifluoromethylacetophenone 6 in 530 ml of pyridine are added 65.4 g (0.282 mol) of amine hydrochloride 4 at 20° C. and the reaction mixture is heated to 90° C. After c. 2 h the reaction is complete and excess pyridine is removed under a water-jet vacuum. The residue is taken up in 600 ml of cold water and the pH is adjusted with concentrated hydrochloric acid to 1–2. After 3 extractions with ethyl acetate, the combined organic phases are washed once with water and once with a 10% solution of sodium carbonate, dried over sodium sulfate, filtered and evaporated to dryness under a water-jet vacuum, giving 101 g of a yellow oil (=98% of theory) that contains pure oxime 7 as an E/Z mixture (E: 87%; Z: 13%) (NMR spectroscopy). The oxime can also be distilled under a fine vacuum; b.p. 168°–178° C./0.1 mbar.

Example 4

(Reaction sequence D)

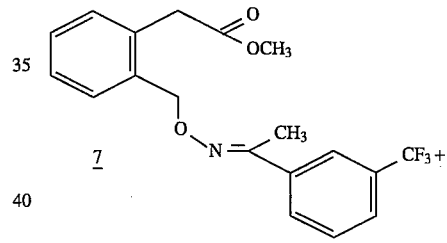

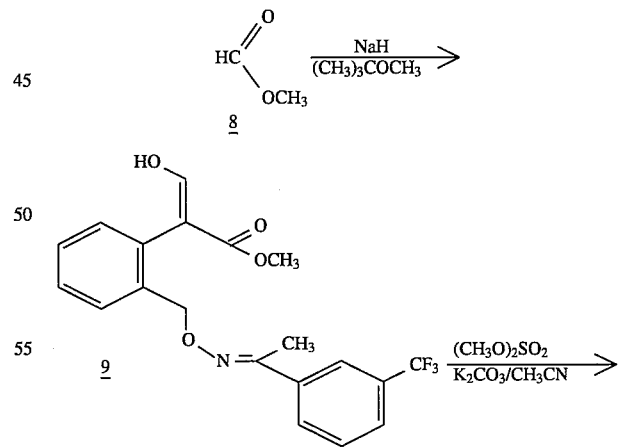

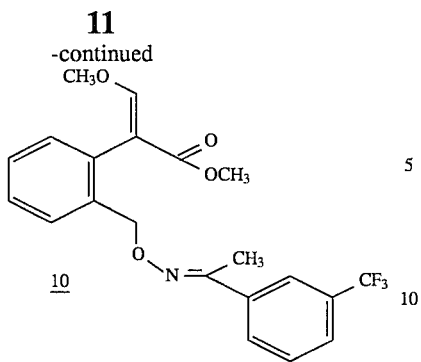

A mixture of 46.0 g (0.125 mol) of oxime ether 7, 31.3 g (0.52 mol) of methyl formate and ml of tert-butylmethyl ether is added dropwise at 29°–35° C. to a suspension 6.7 g (0.28 mol) of sodium hydride in 100 ml of tert-butyl methylether after addition of 0.5 ml of methanol. At the start it is necessary to await the end of a brief induction period. The oxime ether solution is added dropwise over 3 hours. The reaction mixture is thereafter stirred for 5 hours at 30°–35° C. For working up, the reaction mixture is cooled to 0°–5°C. c. 2 ml of methanol and then 100 ml are added dropwise, the pH is adjusted to 5 with c. 20 ml of acetic acid, and the phases are separated. The aqueous phase is extracted twice with 300 ml of tert-butyl methyl ether. The combined organic phases are washed twice with a 5% solution of sodium carbonate, dried over sodium sulfate, filtered and evaporated to dryness, giving 48.3 g (≈98.1% of theory) of a yellow oil 9 which NMR spectroscopy shows to be pure (E/Z mixture).

16.4 g (0.13 mol) of dimethyl sulfate are added dropwise over 30 minutes at 25° C. to a mixture of 48.2 g (0.122 mol) of enol 9, 25.3 g (0.183 mol) of pulverised potassium carbonate in 500 ml of acetonitrile and the mixture is then stirred for 5 h at 25° C. For working up, the acetonitrile is stripped off under vacuum and the residue is taken up in 500 ml of water and 500 ml of toluene. The phases are separated and the aqueous phase is extracted once with 200 ml of toluene. The combined organic phases are washed once with water, evaporated to dryness under vacuum, and finally fully dried at 60° C and 0.13 mbar, giving 48.0 g (≈96.5% of theory) of an orange oil 10 which, according to NMR analysis, contains 89% of E and anti; 8% of E and syn; and 3% of Z-isomer.

Example 5

(Reaction sequence D)

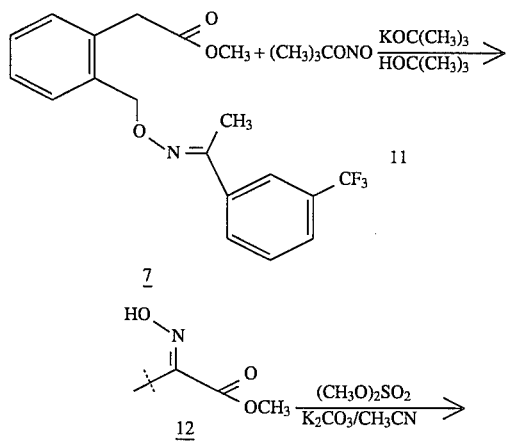

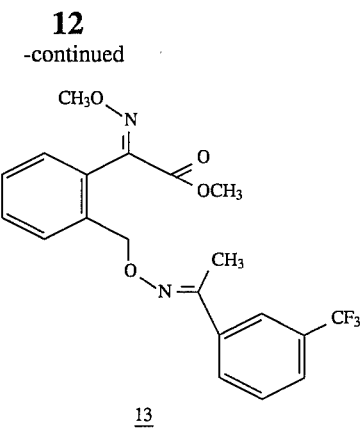

A solution of 5.7 g (15.6 mmol) of oxime ether 7, 6.0 g (52.3 mmol) of tert-butyl nitrite (90%) and 10 ml of tert-butanol is added dropwise at 30° C. over 1 h to a solution of 1.8 g (15.6 mmol) potassium tert-butylate in 15 ml of tert-butanol. The reaction mixture is afterwards stirred for 2 h at 35° C. For working up, the reaction mixture is cooled to 10° C., and 10 ml of water and then 1.2 g of acetic acid are added dropwise. The mixture is then taken up in 200 ml of ethyl acetate, washed with water and evaporated to dryness under a water-jet vacuum, giving 5.2 g of an orange oil 12, which is purified by heating in 25 ml of hexane, whereupon the product begins to crystallise. The batch is cooled to 20° C, filtered with suction, and the pale yellow crystalline product with a melting point of 132°–138° C. is recrystallised from 8 ml of toluene and 1 ml of hexane to give 2.4 g (≈39%) of a white crystalline powder having a melting point of 141°–144° C.

To a mixture of 2.3 g (5.8 mmol) of the oxime 12 obtained above, 1.6 g (11.6 mmol) of pulverised potassium carbonate and 25 ml of acetonitrile are added 0.79 g (6.3 mmol) of dimethyl sulfate at 25° C. After stirring for 3 h, the acetonitrile is stripped off under a water-jet vacuum and the residue is added to water. After two extractions with ethyl acetate, the combined organic phases are washed with water, dried over sodium sulfate, filtered and concentrated by evaporation. The dioxime ether 13 is isolated by chromatography on silica gel with ethyl acetate/hexane (1:2), giving pale yellow crystals with a melting point of 67°–69° C.

Example 6

(Reaction sequence C)

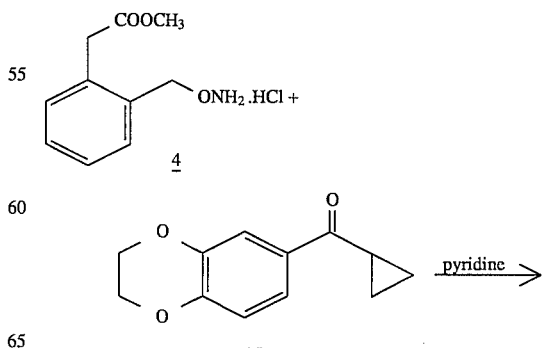

-continued

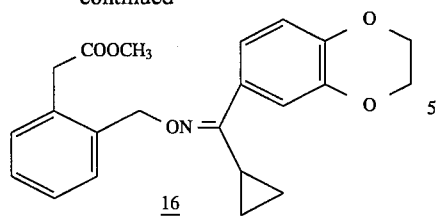

38.8 g of (1,4-benzodioxan-6-yl)cyclopropyl ketone 15 and 44.0 g of 4 are stirred in 400 ml of pyridine for 4 h at 100° C. The solvent is then removed by distillation and the residue is stirred in 0.5 liter of ice-water and 1 liter of diethyl ether. The aqueous phase is separated, the organic phase is washed with water, dried over sodium sulfate and concentrated under vacuum. The residue is chromatographed with dichloromethane on silica gel to give 32 g of 16 as a pale yellow oil, MS: 381 ($M^{+,}$ 12%), 163 (100).

Example 7

(Reaction sequence D)

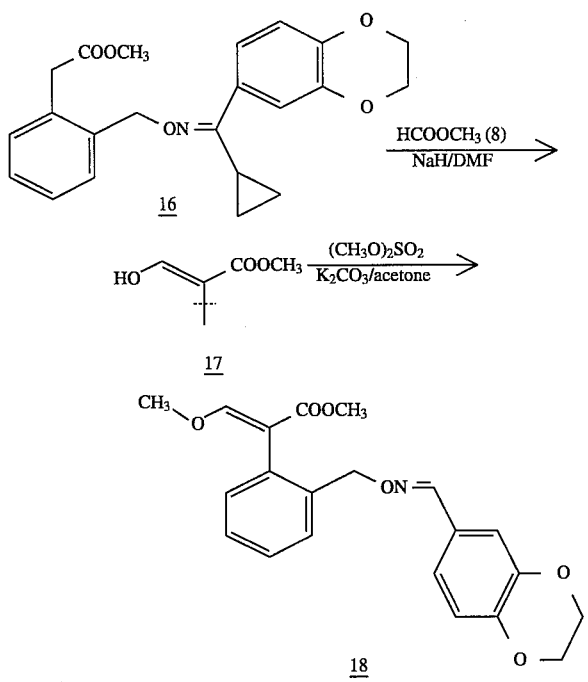

A solution of 39.8 g of methyl {[α-(cyclopropyl-3,4-ethylenedioxybenzyl)imino]oxy}-o-tolylacetate 16 in 100 ml of dimethyl formamide (DMF) and 62 ml of methyl formate is slowly added dropwise to a suspension of 8.0 g of sodium hydride in 300 ml of dimethyl formamide. The reaction mixture is stirred for 3 h at room temperature, acidified with acetic acid and then extracted with diethyl ether. The organic phase is washed twice with water and once with sodium chloride solution, dried over sodium sulfate and concentrated under vacuum, giving crude methyl 2-[α-{[(α-cyclopropyl-3,4-ethylenedioxybenzyl)imino]oxy}-o-tolyl]-3-hydroxy-acrylate 17, which is further reacted without purification.

The above starting material 17, 10.4 ml of dimethyl sulfate, 15.2 g potassium carbonate and 350 ml of acetone are stirred for 2 h at room temperature. The mixture is filtered and the filtrate is concentrated under vacuum, giving a reddish-brown oil. This oil is chromatographed on silica gel with tetrahydrofuran/n-hexane (1:2) to give 30 g of [E]-methyl 2-[α-{[(α-cyclopropyl-3,4-ethylenedioxybenzyl)imino]oxy}-o-tolyl]-3-methoxyacrylate 18 as a yellow oil.

Example 8

(Reaction sequence C)

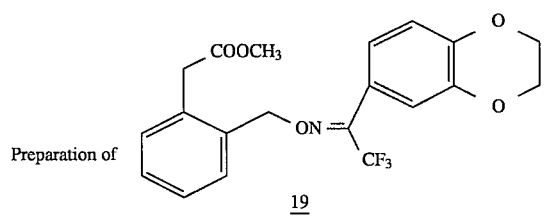

Preparation of

In general accordance with the procedure described in Example 6, reaction of 50.0 g of (1,4-benzodioxan-6-yl)trifluoromethyl ketone and 49.8 g of amine hydrochloride 4 in 420 ml of pyridine gives the ester 19 as a yellow oil.

Example 9

(Reaction sequence D)

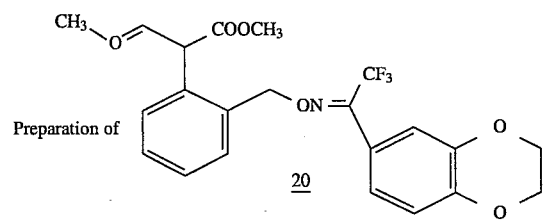

Preparation of

In general accordance with the procedure described in Example 7, the intermediate 19 obtained according to Example 8 in methyl formate is added dropwise to a suspension of NaH in DMF and thus reacted to the methyl hydroxyacrylate, which is then methylated with dimethyl sulfate. Chromatography on silica gel with diethyl ether/n-hexane (1:1) gives methyl 3-methoxy-2-[α{[(α-trifluoromethyl-3,4-ethylenedioxybenzyl)imino]oxy}-o-tolyl]acrylate 20 as a pale yellow oil, MS: 451 ($M^{+,}$ 4%), 145 (100).

Example 10

(Reaction sequence C)

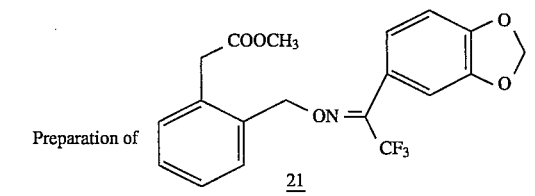

Preparation of

In general accordance with the procedure described in Example 6, the ester 21 is obtained as a yellow oil from 35.0 g of (3,4-methylenedioxyphenyl)trifluoromethyl ketone and 37.5 g of 4.

Example 11

(Reaction sequence D)

Preparation of

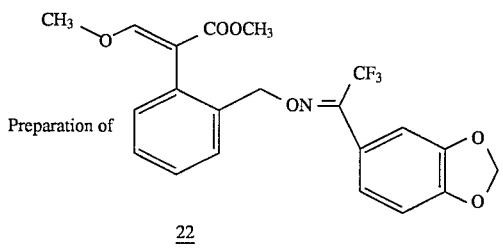

22

In general accordance with the procedure described in Example 7, the intermediate 21 with methyl formate and NaH in DMF give the crude methyl hydroxyacrylate, which is then methylated with dimethyl sulfate to 22. Chromatography on silica gel with diethyl ether/n-hexane (1:2) gives methyl 3-methoxy-2-[α{[(α-trifluoromethyl-3,4-methylenedioxybenzyl)imino]oxy}-o-tolyl]acrylate as a yellow oil, MS: 437 ($M^{+\cdot}$ 1%), 145(100).

Example 12

(Reaction sequence C)

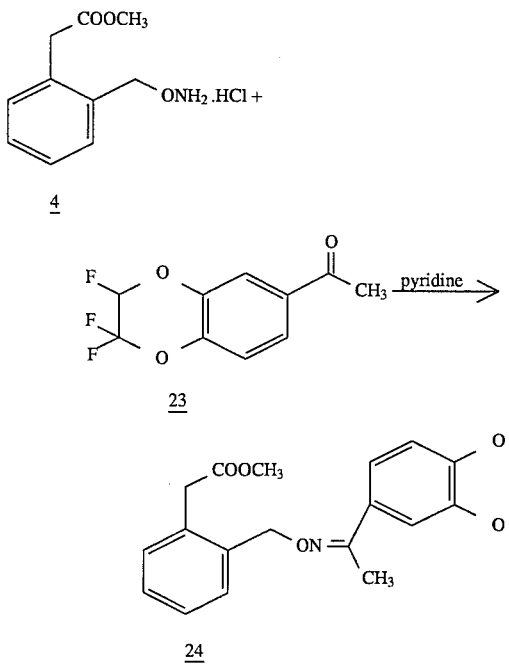

In general accordance with the procedure described in Example 6, the ester 24 is obtained from 80.0 g of the ketone 23 and 79.7 g of amine hydrochloride 4.

Example 13

(Reaction sequence D)

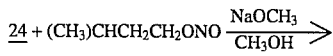

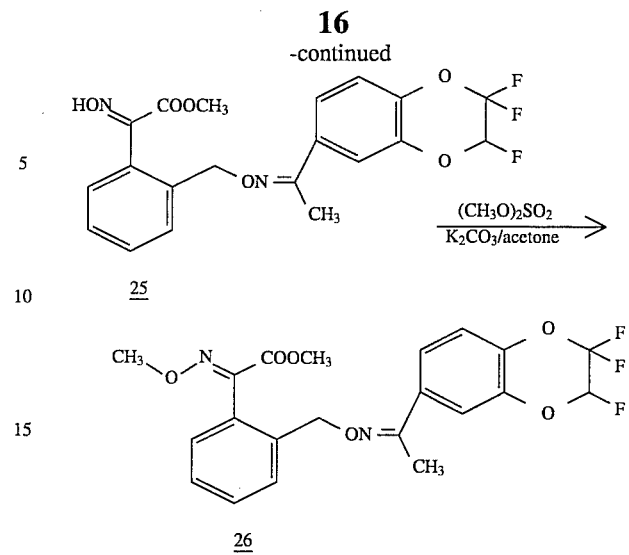

A solution of 50.0 g of the ester 24 obtained according to Example 12 and 24.0 g of isopentyl nitrite in 100 ml of methanol is slowly added dropwise to 34 ml of sodium methylate (30% in methanol). After 2 hours, working up is effected as described in Example 5. The resultant oxime 25 is subsequently methylated with dimethyl sulfate/potassium carbonate in acetone. After chromatography on silica gel (diethyl ether/n-hexane=1:9) and recrystallisation from diethyl ether/n-hexane, 26 is obtained as colourless crystals of m.p. 130°–132° C.

Example 14

(Reaction sequence C)

Preparation of

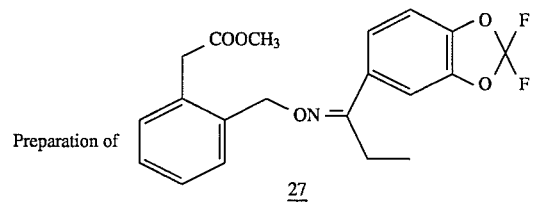

27

In general accordance with the procedure described in Example 6, the ester 27 is obtained as a yellow oil from 58.0 g of 3,4-difluoromethylenedioxypropiophenone and 62.7 g of 4.

Example 15

(Reaction sequence D)

Preparation of

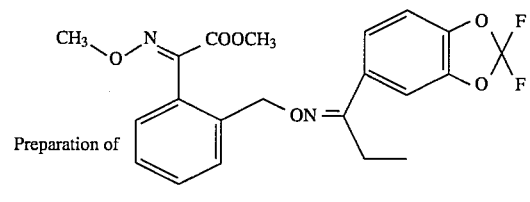

28

In general accordance with the procedure described in Example 13, reaction of 27 with isopentyl nitrite in the presence of sodium methylate in methanol gives the corresponding oxime, which is reacted further with dimethyl sulfate in the presence of $K_2CO_3$/acetone to the dioxime ether 28. The compound 28 with a melting point of m.p.

52°–55° C. crystallises out after chromatography on silica gel (ethyl acetate/n-hexane=1:9).

Example 16

(Reaction sequence C)

Preparation of

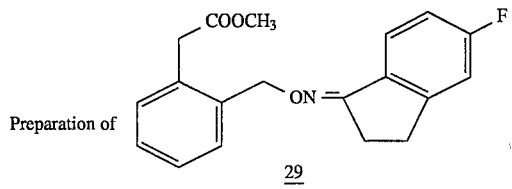

29

In general accordance with the procedure described in Example 6, the ester 29 is obtained from 70.9 g of the aminohydrochloride and 46.0 g of 5-fluoroindan-1-one.

Example 17

(Reaction sequence D)

Preparation of

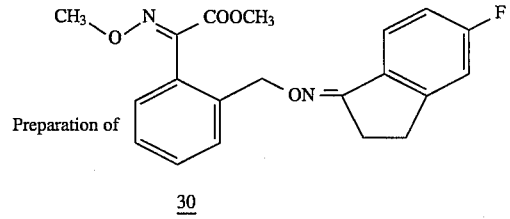

30

In general accordance with the procedure described in Example 13, reaction of the intermediate 29 with a nitrite, e.g. tert-butyl nitrite, gives the corresponding oxime, which is subsequently methylated. Colourless crystals of 30 with a melting point of 89°–92° C. are obtained after chromatography on silica gel (dichloromethane/n-hexane=1:9).

What is claimed is:

1. A 2-aminooxymethylenephenylacetic acid ester derivative of the formula

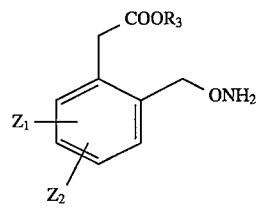

wherein $Z_1$ and $Z_2$ are hydrogen, halogen, hydroxy, $C_1$–$C_4$alkyl, $C_1$–$C_4$alkoxy, $C_1$–$C_4$haloalkyl, $C_1$–$C_4$haloalkoxy, $C_1$–$C_4$alkylcarbonyl, phenoxy, nitro or cyano, or $Z_1$ and $Z_2$, together with the linking phenyl radical, are naphthalene or hydrogenated napthalene, and $R_3$ is hydrogen or $C_1$–$C_{12}$alkyl, as the free base or as a protic acid salt.

2. A compound according to claim 1, wherein $R_3$ is hydrogen or $C_1$–$C_4$alkyl.

3. A compound according to claim 1, wherein $R_3$ is methyl.

* * * * *